(12) United States Patent
Blondel et al.

(10) Patent No.: US 9,351,917 B2
(45) Date of Patent: May 31, 2016

(54) HAIR COMPOSITION WITH IMPROVED RHEOLOGY

(71) Applicant: Conopco, Inc., Englewood Cliffs, NJ (US)

(72) Inventors: Frederic Jean-Michel Blondel, Lezigneux (FR); Christopher John Roberts, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/371,298

(22) PCT Filed: Jan. 29, 2013

(86) PCT No.: PCT/EP2013/051700
§ 371 (c)(1),
(2) Date: Jul. 9, 2014

(87) PCT Pub. No.: WO2013/113705
PCT Pub. Date: Aug. 8, 2013

(65) Prior Publication Data
US 2014/0356306 A1    Dec. 4, 2014

(30) Foreign Application Priority Data

Jan. 31, 2012  (EP) .................................... 12305117

(51) Int. Cl.
*A61K 8/81* (2006.01)
*A61Q 5/12* (2006.01)
*A61Q 5/00* (2006.01)

(52) U.S. Cl.
CPC ............... *A61K 8/8152* (2013.01); *A61Q 5/00* (2013.01); *A61Q 5/12* (2013.01); *A61K 2800/48* (2013.01); *A61K 2800/74* (2013.01)

(58) Field of Classification Search
None
See application file for complete search history.

(56) References Cited

U.S. PATENT DOCUMENTS

| 5,180,473 A | * | 1/1993 | Akune et al. ............... 162/168.2 |
| 2005/0265950 A1 | * | 12/2005 | Chrisstoffels ........ A61K 8/8182 424/70.17 |
| 2008/0264867 A1 | * | 10/2008 | Mika et al. .................... 210/679 |

FOREIGN PATENT DOCUMENTS

| EP | 2116226 A1 | 11/2009 |
| JP | 2001181354 A | * 7/2001 |
| JP | 2002284627 A | * 10/2002 |
| WO | WO9421224 | 9/1994 |
| WO | WO 9934768 A2 | * 7/1999 ............... A61K 8/44 |

OTHER PUBLICATIONS

Zhou et al. Biomaterials 2012 33:2473-2481 available online Dec. 22, 2011.*
Podual et al. Polymer 2000 41:3975-3983.*
Tinovis® CD Rheology Modifier Technical Data Sheet 2010.*
"Fortified Growth Combing Cream", Mintel Abstract, Sep. 1, 2010, (XP002677053) (www.gnpd.com).
"Wonder Serum Spray", Mintel Abstract, Oct. 1, 2010, (XP002677052) (www.gnpd.com).
PCT International Search Report in PCT application PCT/EP2013/051700 dated Mar. 25, 2013.
European Search Report in EP application EP 12 30 5117 dated Jun. 4, 2012.

* cited by examiner

*Primary Examiner* — Robert A Wax
*Assistant Examiner* — Caralynne Helm
(74) *Attorney, Agent, or Firm* — Karen E. Klumas

(57) ABSTRACT

A hair treatment composition comprising a thickener which comprises a copolymer derived from the polymerization of at least a non-ionic monomer (a) and at least a cationic monomer (b).

14 Claims, No Drawings

HAIR COMPOSITION WITH IMPROVED RHEOLOGY

The present invention relates to a hair treatment composition with improved rheology.

Conditioning compositions typically comprise rheology modifiers to maintain good sensorial properties during application. An example is Tinovis CD® which is commercially available from BASF.

Low pH formulations offer enhanced claims for internal repair of damaged hair fibres. Unfortunately, this aspect of hair fibre repair treatment is not possible from compositions comprising the standard rheology modifier Tinovis CD® since the polymer is sensitive to increased levels of electrolyte. The sensitivity manifests itself as a drop in viscosity which has a detrimental effect on the quality of the product.

Accordingly, there remains a need for leave on treatments with improved rheology. The present invention, therefore, provides a hair treatment composition comprising a thickener which comprises a co-polymer derived from the polymerization of at least a non-ionic monomer (a) and at least a cationic monomer (b), wherein the non-ionic monomer (a) is selected from the group consisting of methacrylamide, N-isopropylacrylamide, N-methylolacrylamide, N-vinylformamide, N-vinylpyridine, N-vinylpyrrolidone, 2-hydroxyethylacrylate, poly(ethylene glycol) acrylate, and/or poly(ethylene glycol) methacrylate.

Preferably the non-ionic monomer (a) is poly(ethylene glycol) acrylate, and/or poly(ethylene glycol) methacrylate.

Most preferably, the non-ionic monomer (a) is PEG-methacrylate of the following structure corresponding to Formula I.

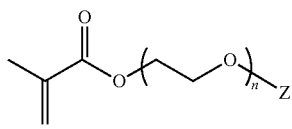

(I)

n is from 1 to 250 and Z is H or an alkyl group with 1 to 5 carbon atoms.

The cationic monomer (b) is selected from the group consisting of acryloyloxyethyltrialkylammonium and/or methacryloyloxyethyltrialkylammonium, quaternized or salified, diallyldimethyl ammonium chloride, acrylamidopropyltrimethylammonium chloride, and/or methacrylamidopropyltrimethylammonium chloride.

Preferably, the cationic monomer (b) is acryloyloxyethyltrialkylammonium and/or methacryloyloxyethyltrialkylammonium, quaternized or salified.

Most preferably, the cationic monomer (b) is methacryloyloxyethyltrialkylammonium salt of the following formula (II)

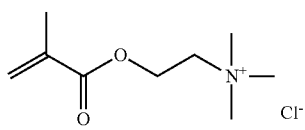

(II)

Preferably, non-ionic monomer represents from 0.1 to 15 mol % of the polymer, without taking into account the crosslinking agent or the chain transfer agent.

Preferably, the cationic monomer represents from 85 to 99.9 mol % of the polymer, without taking into account the crosslinking agent or the chain transfer agent.

Preferably, the polymer is crosslinked with an amount of crosslinking agent comprises between 50 to 5,000 ppm in weight based on the total amount of cationic and non-ionic monomers.

The crosslinking agent is selected from the group comprising methylene bisacrylamide (MBA), ethylene glycol diacrylate, polyethylene glycol dimethacrylate, diacrylamide, cyanomethylacrylate, vinyloxyethylacrylate or methacrylate, triallylamine, formaldehyde, glyoxal, compounds of the glycidylether type such as ethyleneglycol diglycidylether, or epoxy.

A chain transfer agent may be used in the polymerization of the co-polymer of the invention. The chain transfer agent is preferably selected from the group comprising phosphate-type chain transfer agents, such as sodium hypophosphite, lower alcohols, such as methanol or isopropanol, thiol based chain transfer agent, such as 2-mercaptoethanol and mixtures of the foregoing agents.

A preferred embodiment of the present invention is a copolymer derived from the polymerization of (a) 0.1 to 15 mol % of PEG-methacrylate of the following structure corresponding to Formula I.

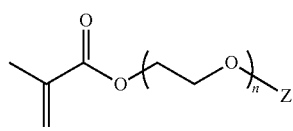

(I)

n is from 1 to 250 and Z is H or an alkyl group with 1 to 5 carbon atoms. And (b) 85 to 99.9 mol % of methacryloyloxyethyltrialkylammonium salt of the following formula (II)

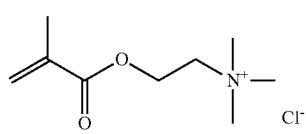

(II)

A more preferred embodiment of the present invention is a copolymer derived from the polymerization of (a) 0.1 to 15 mol % of PEG-methacrylate of the following structure corresponding to Formula I.

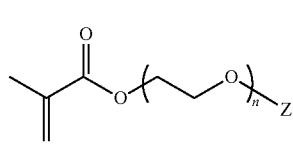

(I)

n is from 1 to 250 and Z is H or an alkyl group with 1 to 5 carbon atoms. And (b) 85 to 99.9 mol % of methacryloyloxyethyltrialkylammonium salt of the following formula (II)

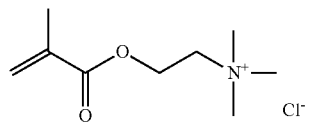
(II)

And (c) 50 to 5,000 ppm (based on the total amount of non-ionic and cationic monomers) of crosslinking agent.

According to the invention, the water-soluble polymers used do not require the development of a particular polymerization method. They can be obtained by all polymerization techniques well known to a person skilled in the art (solution polymerization, suspension polymerization, gel polymerization, precipitation polymerization, emulsion polymerization (aqueous or reverse) followed or not by a spray drying step, suspension polymerization, micellar polymerization followed or not by a precipitation step).

According to one advantageous aspect of the invention, the polymer is made by reverse phase polymerisation for instance as is described generally in U.S. Pat. No. 4,059,552.

An inverse emulsion polymerization process usually comprises the following steps:
A) forming a water-in-oil emulsion of an aqueous solution containing the monomers and/or the crosslinking agent and/or the transfert agent and an emulsifying agent, wherein said emulsifying agent preferably should have an HLB value in the range of 3 to 8 and more preferably in the range of 4 to 6, in a hydrophobic phase, like an oil selected form the group comprising mineral oils, synthetic oils, vegetable oils, silicone oils and mixtures thereof;
and B) polymerizing said monomers to form a polymer emulsion, optionally, by using a free radical generating catalyst to initiate the reaction, and controlling the temperature of the reaction mixture.

The resulting inverse emulsion polymer composition according to the present invention may have an active polymer concentration of about 25 to about 75% by weight.

The inverse emulsion composition according to the present invention may further comprise an inverting surfactant in a concentration of up to about 5 weight percent. The inverting surfactant may improve the polymer's dissolution in water. Suitable inverting surfactants are those with an HLB of at least about 10, preferably 10 to 20, with an HLB of about 10 to about 15 being most preferred. Especially suitable are the non-ionic inverting surfactants. Typical "inverting agents" include fatty alcohol ethoxylates, fatty acid esters-sorbitan-poly ethylene glycols-glycerol, alkyl polyglucosides, etc. Certain silicone compounds such as dimethicone copolyols can also be used.

According to the present invention, it is also possible to concentrate (by heating under vacuum to remove excess water and organic solvent by distillation) or to isolate the polymer by all known techniques. In particular, there are many processes for obtaining a powder on the basis of soluble polymer emulsions or ones which swell in water. These processes involve the isolation of the active matter from other constituents of the emulsion. Such processes include: precipitation in a non-solvent medium such as acetone, methanol, and other polar solvents: simple filtration then permits isolation of the polymer particle, azeotropic distillation in the presence of an agglomerating agent and stabilizing polymer which makes it possible to obtain agglomerates which are easily isolated by filtration before drying of the particle is undertaken, "Spray drying", or drying by atomization or pulverization, which consists of creating a cloud of fine droplets of emulsion in a stream of hot air for a controlled period.

While the present invention has been described with respect to specific embodiments thereof, it will be recognized by those of ordinary skill in the art that many modifications, enhancements, and/or changes can be achieved without departing from the spirit and scope of the invention.

Preferably, the composition comprises from 0.01 to 5% wt. of the composition, more preferably from 0.1 to 1% and most preferably from 0.15 to 0.3% wt. of the composition.

The compositions according to the invention are preferably leave-on conditioning compositions. By conditioning composition is meant compositions which have as their primary object conditioning keratinous fibre, such as hair, as opposed to compositions which have as their primary aim cleansing the hair while providing a conditioning benefit. Accordingly, it is preferred that the composition comprises less than 5% wt. anionic surfactant, more preferably less than 5% wt. cleansing surfactant. More preferably, the composition comprises less than 3% wt. anionic surfactant, still more preferably less than 3% wt. cleansing surfactant and especially preferably no anionic surfactant.

By leave-on composition is meant that the composition is applied to the hair and not rinsed-off. Typically, this is applied to the hair before the user goes to bed at night.

The composition according to the invention comprises from 0.001 to 5% wt. conditioning active, more preferably from 0.1 to 4.0% by wt. conditioning active.

Preferably, the composition comprises a conditioning active selected from acid neutralized amidoamine surfactant, fatty alcohols and conditioning silicones.

Preferably, the acid neutralized amidoamine surfactant is of general formula:

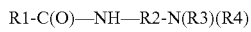

wherein R1 is a fatty acid chain with from 12 to 22 carbon atoms, R2 is an alkylene group containing from one to 4 carbon atoms and R3 and R4 are, independently, an alkyl group having from one to four carbon atoms.

Preferably, the acid neutralized amidoamine surfactant is selected from stearamidopropyl dimethylamine, stearamidopropyl diethylamine, stearamidoethyl dimethylamine, stearamidoethyl diethylamine, palimtamidopropyl dimethylamine, behenamidopropyl dimethylamine, myristamidopropyl dimethylamine, oleoamidopropyl dimethylamine, ricinoleoamidopropyl dimethylamine and mixtures.

Preferably, the composition according to the invention comprises less than 0.5% wt. cationic surfactant. More preferably, the composition according to the invention comprises less than 0.2% wt. cationic surfactant.

Preferably, the composition according to the invention comprises less than 0.5% wt. and more preferably less than 0.2% wt. a cationic surfactant selected from cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18.

Conditioners of the invention advantageously incorporate a fatty alcohol material. The combined use of fatty alcohol materials and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol material in conditioners of the invention is conveniently from 0.01 to 5%, preferably from 0.1 to 3% by weight of the composition.

Silicone is a particularly preferred ingredient in hair treatment compositions of the invention. In particular, conditioners of the invention will preferably also comprise emulsified particles of silicone, for enhancing conditioning performance. The silicone is insoluble in the aqueous matrix of the composition and so is present in an emulsified form, with the silicone present as dispersed particles.

Suitable silicones include polydiorganosiloxanes, in particular polydimethylsiloxanes which have the CTFA designation dimethicone. Also suitable for use compositions of the invention are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning.

The viscosity of the emulsified silicone itself (not the emulsion or the final hair conditioning composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in conditioners of the invention will typically have an average silicone particle size in the composition of less than 30, preferably less than 20, more preferably less than 10 microns. We have found that reducing the particle size generally improves conditioning performance. Most preferably the average silicone particle size of the emulsified silicone in the composition is less than 2 microns, ideally it ranges from 0.01 to 1 micron. Silicone emulsions having an average silicone particle size of ≤0.15 microns are generally termed microemulsions.

Particle size may be measured by means of a laser light scattering technique, using a 2600D Particle Sizer from Malvern Instruments.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in conditioners of the invention are amino functional silicones. By "amino functional silicone" is meant a silicone containing at least one primary, secondary or tertiary amine group, or a quaternary ammonium group.

Examples of suitable amino functional silicones include:
(i) polysiloxanes having the CTFA designation "amodimethicone", and the general formula:

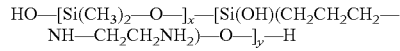

in which x and y are numbers depending on the molecular weight of the polymer, generally such that the molecular weight is between about 5,000 and 500,000.
(ii) polysiloxanes having the general formula:

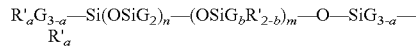

in which:
G is selected from H, phenyl, OH or $O_{1-8}$ alkyl, e.g. methyl;
a is 0 or an integer from 1 to 3, preferably 0;
b is 0 or 1, preferably 1;
m and n are numbers such that (m+n) can range from 1 to 2000, preferably from 50 to 150;
m is a number from 1 to 2000, preferably from 1 to 10;
n is a number from 0 to 1999, preferably from 49 to 149, and
R' is a monovalent radical of formula —$C_qH_{2q}$L in which q is a number from 2 to 8 and L is an aminofunctional group selected from the following:

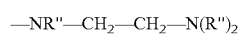

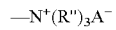

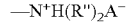

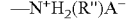

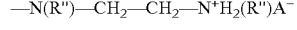

in which R" is selected from H, phenyl, benzyl, or a saturated monovalent hydrocarbon radical, e.g. $C_{1-20}$ alkyl, and;
A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

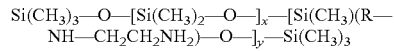

wherein x+y is a number from about 50 to about 500, and wherein R is an alkylene group having from 2 to 5 carbon atoms. Preferably, the number x+y is in the range of from about 100 to about 300.
(iii) quaternary silicone polymers having the general formula:

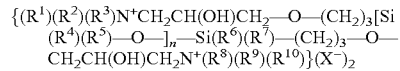

wherein $R^1$ and $R^{10}$ may be the same or different and may be independently selected from H, saturated or unsaturated long or short chain alk(en)yl, branched chain alk(en)yl and $C_5$-$C_8$ cyclic ring systems;
$R^2$ thru' $R^9$ may be the same or different and may be independently selected from H, straight or branched chain lower alk(en)yl, and $C_5$-$C_8$ cyclic ring systems;

n is a number within the range of about 60 to about 120, preferably about 80, and X⁻ is preferably acetate, but may instead be for example halide, organic carboxylate, organic sulphonate or the like.

Suitable quaternary silicone polymers of this class are described in EP-A-0 530 974.

Amino functional silicones suitable for use in conditioners of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with non ionic and/or cationic surfactant.

Suitably such pre-formed emulsions will have an average amino functional silicone particle size in the composition of less than 30, preferably less than 20, more preferably less than 10 microns. Again, we have found that reducing the particle size generally improves conditioning performance. Most preferably the average amino functional silicone particle size in the composition is less than 2 microns, ideally it ranges from 0.01 to 1 micron. Silicone emulsions having an average silicone particle size of ≤0.15 microns are generally termed microemulsions.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

The total amount of silicone incorporated into compositions of the invention depends on the level of conditioning desired and the material used. A preferred amount is from 0.01 to about 5% by weight of the total composition although these limits are not absolute. The lower limit is determined by the minimum level to achieve conditioning and the upper limit by the maximum level to avoid making the hair and/or skin unacceptably greasy.

We have found that a total amount of silicone of from 0.3 to 4%, preferably 0.5 to 3%, by weight of the total composition is a suitable level.

Other ingredients may include viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

free fatty acids, for cuticle repair and damage prevention. Examples are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. A preferred fatty acid is oleic acid. The fatty acids may be added singly, as mixtures, or in the form of blends derived from extracts of, e.g. lanolin.

Mixtures of any of the above active ingredients may also be used.

Preferably, the composition is a leave-on conditioning composition.

Preferably, the composition of the invention has a pH of from 2 to 6, more preferably, from 3 to 5.

In a second aspect there is provided the use of a composition according to any preceding claim for conditioning the hair.

EXAMPLE 1

| Ingredient | % wt. |
|---|---|
| Water | To 100 |
| Lactic acid | 0.1 |
| Stearamidopropyl dimethylamine | 1.0 |
| Fatty alcohol | 3.0 |
| Preservative | 0.2 |
| Mineral oil | 3.0 |
| Dimethicone | 2.0 |
| PQ-37 and acrylamide** | 0.25 |
| Glycerine | 2.0 |
| MQ resin | 0.4 |

* Tinovis CD ex. BASF

EXAMPLE 2

| Ingredient | % wt. |
|---|---|
| Water | To 100 |
| Lactic acid | 0.1 |
| Stearamidopropyl dimethylamine | 1.0 |
| Fatty alcohol | 3.0 |
| Preservative | 0.2 |
| Mineral oil | 3.0 |
| Dimethicone | 2.0 |

-continued

| Ingredient | % wt. |
|---|---|
| Copolymer of methacryloyloxyethyltrialkylammonium salt and PEG methacrylate* | 0.25 |
| Glycerine | 2.0 |
| MQ resin | 0.4 |

*The crosslinked copolymer is in inverse emulsion form, methacryloyloxyethyltrialkylammonium salt and PEG methacrylate represent respectively 98 mol % 2 mol % of the total amount of these two monomers.

EXAMPLE 3

Study of Combing Cream Formulations Under Low pH Conditions

Formulations according to Examples 1 and 2 were pH adjusted using Lactic Acid to achieve set target pH values of 5.5, 5.0, 4.5, 4.0, 3.5 and 3.0 (all +/−0.15 pH units). Natural pH was used as the control Rheology measurements were all conducted using a Bohlin C-VOR rheometer fitted with a serrated cup and bob geometry (C14 DIN 53019). Range of shear rate employed was from $0.001\ s^{-1}$-$1000\ s^{-1}$. Measurements were carried out at 25° C.

The gap between the tips of the cup and bob serrations was 700 μm and the measurements were made in 'controlled rate' mode (stress is continuously adjusted to achieve an actual shear rate that is close to the target shear rate).

No pre-shear was applied to the samples with the shear rate being cycled (Up-Down-Up) in logarithmic steps with 8 pts per decade (Purpose of cycling is to check for any irreversible shear induced changes).

Data was taken from the $2^{nd}$ 'Up' Cycle to ensure a consistent baseline.

Shear Rate vs Normalised Viscosity and Shear-Stress vs Normalised Viscosity plots were generated to compare the samples rheological behaviour.

EXAMPLE 4

| Results - Natural PQ-37 and acrylate ||||
|---|---|---|---|
| Shear Rate (1/s) | Shear Stress (Pa) | Viscosity (Pas) | Visc/Visc@1000 s−1 |
| 0.001 | 13.047 | 13045.000 | 41012.985 |
| 0.002 | 22.902 | 12884.000 | 40506.807 |
| 0.003 | 33.328 | 10540.000 | 33137.360 |
| 0.006 | 42.199 | 7507.100 | 23602.037 |
| 0.010 | 47.850 | 4786.400 | 15048.260 |
| 0.018 | 50.778 | 2856.200 | 8979.784 |
| 0.032 | 50.963 | 1612.200 | 5068.696 |
| 0.056 | 51.450 | 915.390 | 2877.951 |
| 0.100 | 52.668 | 526.940 | 1656.679 |
| 0.178 | 54.256 | 305.230 | 959.632 |
| 0.316 | 56.229 | 177.880 | 559.248 |
| 0.562 | 58.259 | 103.640 | 325.840 |
| 1.000 | 60.364 | 60.385 | 189.848 |
| 1.778 | 62.619 | 35.228 | 110.755 |
| 3.161 | 65.479 | 20.716 | 65.130 |
| 5.621 | 69.129 | 12.298 | 38.664 |
| 9.997 | 74.044 | 7.407 | 23.287 |
| 17.777 | 80.910 | 4.552 | 14.310 |
| 31.611 | 90.040 | 2.848 | 8.955 |
| 56.207 | 102.700 | 1.827 | 5.745 |
| 99.950 | 119.540 | 1.196 | 3.760 |
| 177.750 | 142.570 | 0.802 | 2.522 |

| Results - Natural PQ-37 and acrylate ||||
|---|---|---|---|
| Shear Rate (1/s) | Shear Stress (Pa) | Viscosity (Pas) | Visc/Visc@1000 s−1 |
| 316.120 | 173.340 | 0.548 | 1.724 |
| 562.140 | 228.750 | 0.407 | 1.279 |
| 999.660 | 317.960 | 0.318 | 1.000 |

| Natural PQ-37 and acrylamide ||||
|---|---|---|---|
| Shear Rate (1/s) | Shear Stress (Pa) | Viscosity (Pas) | Visc/Visc@1000 s−1 |
| 0.001 | 10.678 | 10671.000 | 41644.552 |
| 0.002 | 20.973 | 11792.000 | 46019.357 |
| 0.003 | 22.385 | 7081.400 | 27635.810 |
| 0.006 | 21.753 | 3870.000 | 15103.028 |
| 0.010 | 21.861 | 2186.800 | 8534.187 |
| 0.018 | 22.096 | 1243.000 | 4850.921 |
| 0.032 | 22.532 | 712.820 | 2781.845 |
| 0.056 | 23.277 | 414.080 | 1615.985 |
| 0.100 | 24.339 | 243.510 | 950.320 |
| 0.178 | 25.910 | 145.760 | 568.842 |
| 0.316 | 28.024 | 88.652 | 345.973 |
| 0.562 | 30.499 | 54.255 | 211.735 |
| 1.000 | 33.014 | 33.028 | 128.895 |
| 1.777 | 35.913 | 20.205 | 78.852 |
| 3.161 | 39.215 | 12.407 | 48.419 |
| 5.621 | 43.421 | 7.724 | 30.145 |
| 9.996 | 48.964 | 4.898 | 19.116 |
| 17.777 | 55.880 | 3.143 | 12.267 |
| 31.612 | 64.889 | 2.053 | 8.011 |
| 56.207 | 77.532 | 1.379 | 5.383 |
| 99.950 | 93.462 | 0.935 | 3.649 |
| 177.750 | 114.110 | 0.642 | 2.505 |
| 316.100 | 144.170 | 0.456 | 1.780 |
| 562.110 | 192.000 | 0.342 | 1.333 |
| 999.640 | 256.150 | 0.256 | 1.000 |

| pH 5.5 PQ-37 and acrylate ||||
|---|---|---|---|
| Shear Rate (1/s) | Shear Stress (Pa) | Viscosity (Pas) | Visc/Visc@1000 s−1 |
| 0.001 | 9.571 | 9562.200 | 41836.717 |
| 0.002 | 18.855 | 10602.000 | 46386.069 |
| 0.003 | 23.053 | 7291.700 | 31902.783 |
| 0.006 | 23.555 | 4190.700 | 18335.229 |
| 0.010 | 24.125 | 2413.600 | 10560.028 |
| 0.018 | 24.829 | 1396.800 | 6111.306 |
| 0.032 | 25.788 | 815.770 | 3569.172 |
| 0.056 | 26.921 | 478.950 | 2095.511 |
| 0.100 | 28.306 | 283.200 | 1239.062 |
| 0.178 | 29.948 | 168.480 | 737.137 |
| 0.316 | 31.767 | 100.490 | 439.666 |
| 0.562 | 33.748 | 60.035 | 262.666 |
| 1.000 | 35.862 | 35.875 | 156.961 |
| 1.777 | 38.447 | 21.631 | 94.640 |
| 3.161 | 41.499 | 13.129 | 57.442 |
| 5.621 | 45.375 | 8.072 | 35.317 |
| 9.996 | 50.371 | 5.039 | 22.046 |
| 17.777 | 56.807 | 3.196 | 13.981 |
| 31.612 | 65.164 | 2.061 | 9.019 |
| 56.211 | 76.732 | 1.365 | 5.973 |
| 99.950 | 91.197 | 0.912 | 3.992 |
| 177.750 | 111.600 | 0.628 | 2.747 |
| 316.120 | 143.760 | 0.455 | 1.990 |
| 562.120 | 177.410 | 0.316 | 1.381 |
| 999.640 | 228.480 | 0.229 | 1.000 |

| pH 5.5 PQ-37 and acrylamide | | | |
|---|---|---|---|
| Shear Rate (1/s) | Shear Stress (Pa) | Viscosity (Pas) | Visc/Visc@1000 s−1 |
| 0.001 | 3.932 | 3933.900 | 23505.617 |
| 0.002 | 7.129 | 4010.200 | 23961.520 |
| 0.003 | 7.612 | 2408.400 | 14390.535 |
| 0.006 | 7.813 | 1389.900 | 8304.852 |
| 0.010 | 8.085 | 808.820 | 4832.815 |
| 0.018 | 8.440 | 474.790 | 2836.938 |
| 0.032 | 8.869 | 280.570 | 1676.446 |
| 0.056 | 9.412 | 167.450 | 1000.538 |
| 0.100 | 10.087 | 100.920 | 603.011 |
| 0.178 | 10.933 | 61.506 | 367.507 |
| 0.316 | 11.939 | 37.766 | 225.657 |
| 0.562 | 13.143 | 23.380 | 139.699 |
| 1.000 | 14.566 | 14.571 | 87.064 |
| 1.778 | 16.260 | 9.148 | 54.658 |
| 3.161 | 18.205 | 5.759 | 34.413 |
| 5.621 | 20.660 | 3.676 | 21.962 |
| 9.996 | 23.772 | 2.378 | 14.209 |
| 17.776 | 27.886 | 1.569 | 9.373 |
| 31.612 | 33.409 | 1.057 | 6.315 |
| 56.207 | 41.352 | 0.736 | 4.396 |
| 99.950 | 51.958 | 0.520 | 3.106 |
| 177.750 | 65.827 | 0.370 | 2.213 |
| 316.120 | 92.591 | 0.293 | 1.750 |
| 562.120 | 118.800 | 0.211 | 1.263 |
| 999.640 | 167.300 | 0.167 | 1.000 |

| pH 5.0 PQ-37 and acrylate | | | |
|---|---|---|---|
| Shear Rate (1/s) | Shear Stress (Pa) | Viscosity (Pas) | Visc/Visc@1000 s−1 |
| 0.001 | 2.575 | 2581.200 | 37363.751 |
| 0.002 | 5.559 | 3119.600 | 45157.275 |
| 0.003 | 7.277 | 2304.900 | 33364.214 |
| 0.006 | 6.829 | 1214.400 | 17578.854 |
| 0.010 | 6.668 | 666.980 | 9654.763 |
| 0.018 | 6.177 | 347.480 | 5029.892 |
| 0.032 | 6.618 | 209.380 | 3030.847 |
| 0.056 | 6.257 | 111.300 | 1611.105 |
| 0.100 | 6.148 | 61.509 | 890.364 |
| 0.178 | 6.402 | 36.017 | 521.358 |
| 0.316 | 6.705 | 21.211 | 307.036 |
| 0.562 | 7.005 | 12.462 | 180.392 |
| 1.000 | 7.289 | 7.292 | 105.553 |
| 1.777 | 7.856 | 4.420 | 63.981 |
| 3.161 | 8.494 | 2.687 | 38.898 |
| 5.621 | 9.371 | 1.667 | 24.130 |
| 9.997 | 11.067 | 1.107 | 16.026 |
| 17.776 | 12.666 | 0.713 | 10.314 |
| 31.612 | 14.029 | 0.444 | 6.424 |
| 56.207 | 18.649 | 0.332 | 4.803 |
| 99.950 | 21.743 | 0.218 | 3.149 |
| 177.750 | 26.168 | 0.147 | 2.131 |
| 316.100 | 37.016 | 0.117 | 1.695 |
| 562.150 | 48.760 | 0.087 | 1.256 |
| 999.660 | 69.059 | 0.069 | 1.000 |

| pH 5.0 PQ-37 and acrylamide | | | |
|---|---|---|---|
| Shear Rate (1/s) | Shear Stress (Pa) | Viscosity (Pas) | Visc/Visc@1000 s−1 |
| 0.001 | 7.842 | 7850.500 | 38224.267 |
| 0.002 | 15.493 | 8711.500 | 42416.496 |
| 0.003 | 19.161 | 6061.800 | 29515.045 |
| 0.006 | 19.731 | 3510.100 | 17090.759 |
| 0.010 | 20.326 | 2033.100 | 9899.211 |
| 0.018 | 21.064 | 1184.900 | 5769.306 |
| 0.032 | 21.911 | 693.180 | 3375.110 |
| 0.056 | 22.938 | 408.070 | 1986.902 |
| 0.100 | 24.192 | 242.040 | 1178.498 |
| 0.178 | 25.659 | 144.350 | 702.844 |
| 0.316 | 27.353 | 86.528 | 421.307 |
| 0.562 | 29.198 | 51.941 | 252.902 |
| 1.000 | 31.249 | 31.262 | 152.215 |
| 1.777 | 33.590 | 18.897 | 92.010 |
| 3.161 | 36.514 | 11.552 | 56.247 |
| 5.621 | 39.960 | 7.109 | 34.613 |
| 9.997 | 44.638 | 4.465 | 21.742 |
| 17.776 | 50.358 | 2.833 | 13.793 |
| 31.612 | 58.171 | 1.840 | 8.960 |
| 56.207 | 68.587 | 1.220 | 5.942 |
| 99.950 | 82.688 | 0.827 | 4.028 |
| 177.750 | 100.630 | 0.566 | 2.756 |
| 316.100 | 134.990 | 0.427 | 2.079 |
| 562.150 | 160.310 | 0.285 | 1.389 |
| 999.660 | 205.310 | 0.205 | 1.000 |

| pH 4.5 PQ-37 and acrylate | | | |
|---|---|---|---|
| Shear Rate (1/s) | Shear Stress (Pa) | Viscosity (Pas) | Visc/Visc@1000 s−1 |
| 0.001 | 7.579 | 7571.600 | 34505.765 |
| 0.002 | 15.080 | 8485.200 | 38669.279 |
| 0.003 | 18.681 | 5910.700 | 26936.608 |
| 0.006 | 19.413 | 3453.500 | 15738.504 |
| 0.010 | 20.080 | 2008.700 | 9154.172 |
| 0.018 | 20.854 | 1173.200 | 5346.580 |
| 0.032 | 21.766 | 688.550 | 3137.903 |
| 0.056 | 22.852 | 406.570 | 1852.846 |
| 0.100 | 24.160 | 241.720 | 1101.581 |
| 0.178 | 25.694 | 144.550 | 658.752 |
| 0.316 | 27.433 | 86.785 | 395.502 |
| 0.562 | 29.295 | 52.113 | 237.493 |
| 1.000 | 31.362 | 31.373 | 142.975 |
| 1.777 | 33.533 | 18.866 | 85.977 |
| 3.161 | 35.924 | 11.365 | 51.793 |
| 5.621 | 39.422 | 7.013 | 31.961 |
| 9.996 | 44.229 | 4.425 | 20.165 |
| 17.777 | 50.317 | 2.831 | 12.899 |
| 31.610 | 59.352 | 1.878 | 8.557 |
| 56.207 | 69.492 | 1.236 | 5.635 |
| 99.950 | 84.282 | 0.843 | 3.843 |
| 177.750 | 103.870 | 0.584 | 2.663 |
| 316.120 | 131.070 | 0.415 | 1.889 |
| 562.150 | 167.020 | 0.297 | 1.354 |
| 999.640 | 219.350 | 0.219 | 1.000 |

| pH 4.5 PQ-37 and acrylamide | | | |
|---|---|---|---|
| Shear Rate (1/s) | Shear Stress (Pa) | Viscosity (Pas) | Visc/Visc@1000 s−1 |
| 0.001 | 3.758 | 3757.700 | 22084.631 |
| 0.002 | 6.785 | 3819.300 | 22446.665 |
| 0.003 | 7.223 | 2286.700 | 13439.318 |
| 0.006 | 7.401 | 1316.900 | 7739.641 |
| 0.010 | 7.758 | 775.910 | 4560.153 |
| 0.018 | 8.094 | 455.300 | 2675.874 |
| 0.032 | 8.449 | 267.250 | 1570.673 |
| 0.056 | 9.032 | 160.670 | 944.284 |
| 0.100 | 9.690 | 96.947 | 569.774 |
| 0.178 | 10.554 | 59.374 | 348.951 |
| 0.316 | 11.574 | 36.616 | 215.198 |
| 0.562 | 12.831 | 22.824 | 134.140 |
| 1.000 | 14.229 | 14.235 | 83.661 |

| pH 4.5 PQ-37 and acrylamide | | | |
|---|---|---|---|
| Shear Rate (1/s) | Shear Stress (Pa) | Viscosity (Pas) | Visc/Visc@1000 s−1 |
| 1.777 | 15.963 | 8.981 | 52.783 |
| 3.161 | 17.853 | 5.648 | 33.196 |
| 5.621 | 20.230 | 3.599 | 21.151 |
| 9.996 | 23.414 | 2.342 | 13.766 |
| 17.777 | 27.520 | 1.548 | 9.098 |
| 31.612 | 33.192 | 1.050 | 6.171 |
| 56.207 | 41.052 | 0.730 | 4.292 |
| 99.950 | 51.860 | 0.519 | 3.049 |
| 177.750 | 66.470 | 0.374 | 2.198 |
| 316.120 | 83.256 | 0.263 | 1.548 |
| 562.110 | 125.050 | 0.222 | 1.307 |
| 999.640 | 170.090 | 0.170 | 1.000 |

| pH 4.0 PQ-37 and acrylate | | | |
|---|---|---|---|
| Shear Rate (1/s) | Shear Stress (Pa) | Viscosity (Pas) | Visc/Visc@1000 s−1 |
| 0.001 | 7.753 | 7752.000 | 35186.782 |
| 0.002 | 15.227 | 8565.500 | 38879.306 |
| 0.003 | 18.501 | 5852.300 | 26563.933 |
| 0.006 | 19.118 | 3400.100 | 15433.253 |
| 0.010 | 19.779 | 1978.500 | 8980.527 |
| 0.018 | 20.599 | 1158.700 | 5259.407 |
| 0.032 | 21.511 | 680.500 | 3088.829 |
| 0.056 | 22.609 | 402.230 | 1825.746 |
| 0.100 | 24.003 | 240.130 | 1089.964 |
| 0.178 | 25.607 | 144.060 | 653.897 |
| 0.316 | 27.505 | 87.013 | 394.957 |
| 0.562 | 29.701 | 52.838 | 239.835 |
| 1.000 | 32.004 | 32.017 | 145.327 |
| 1.778 | 34.620 | 19.476 | 88.403 |
| 3.161 | 37.700 | 11.927 | 54.137 |
| 5.621 | 41.485 | 7.380 | 33.499 |
| 9.997 | 46.487 | 4.650 | 21.108 |
| 17.777 | 52.807 | 2.971 | 13.484 |
| 31.612 | 61.133 | 1.934 | 8.778 |
| 56.207 | 72.415 | 1.288 | 5.848 |
| 99.950 | 87.157 | 0.872 | 3.958 |
| 177.750 | 106.830 | 0.601 | 2.728 |
| 316.100 | 142.040 | 0.449 | 2.040 |
| 562.150 | 169.090 | 0.301 | 1.365 |
| 999.640 | 220.230 | 0.220 | 1.000 |

| pH 4.0 PQ-37 and acrylamide | | | |
|---|---|---|---|
| Shear Rate (1/s) | Shear Stress (Pa) | Viscosity (Pas) | Visc/Visc@1000 s−1 |
| 0.001 | 2.975 | 2972.900 | 17833.833 |
| 0.002 | 5.376 | 3026.600 | 18155.969 |
| 0.003 | 5.612 | 1775.900 | 10653.269 |
| 0.006 | 5.756 | 1024.400 | 6145.171 |
| 0.010 | 5.970 | 597.190 | 3582.424 |
| 0.018 | 6.217 | 349.740 | 2098.121 |
| 0.032 | 6.542 | 206.940 | 1241.392 |
| 0.056 | 6.974 | 124.070 | 744.271 |
| 0.100 | 7.513 | 75.157 | 450.852 |
| 0.178 | 8.231 | 46.302 | 277.756 |
| 0.316 | 9.146 | 28.933 | 173.563 |
| 0.562 | 10.317 | 18.355 | 110.108 |
| 1.000 | 11.760 | 11.765 | 70.576 |
| 1.778 | 13.523 | 7.608 | 45.638 |
| 3.161 | 15.399 | 4.872 | 29.226 |
| 5.621 | 17.730 | 3.154 | 18.921 |
| 9.996 | 20.667 | 2.068 | 12.403 |
| 17.776 | 24.487 | 1.378 | 8.263 |
| 31.612 | 29.985 | 0.949 | 5.690 |
| 56.207 | 38.970 | 0.693 | 4.159 |
| 99.950 | 49.764 | 0.498 | 2.987 |
| 177.750 | 63.835 | 0.359 | 2.154 |
| 316.120 | 91.541 | 0.290 | 1.737 |
| 562.150 | 130.330 | 0.232 | 1.391 |

| pH 3.5 PQ-37 and acrylate | | | |
|---|---|---|---|
| Shear Rate (1/s) | Shear Stress (Pa) | Viscosity (Pas) | Visc/Visc@1000 s−1 |
| 0.001 | 7.731 | 7723.200 | 34381.872 |
| 0.002 | 15.227 | 8564.500 | 38127.142 |
| 0.003 | 18.386 | 5816.400 | 25893.247 |
| 0.006 | 19.067 | 3392.100 | 15100.832 |
| 0.010 | 19.754 | 1976.200 | 8797.578 |
| 0.018 | 20.563 | 1156.700 | 5149.357 |
| 0.032 | 21.451 | 678.610 | 3021.012 |
| 0.056 | 22.563 | 401.420 | 1787.028 |
| 0.100 | 23.931 | 239.420 | 1065.842 |
| 0.178 | 25.506 | 143.490 | 638.784 |
| 0.316 | 27.350 | 86.523 | 385.180 |
| 0.562 | 29.360 | 52.228 | 232.507 |
| 1.000 | 31.528 | 31.540 | 140.409 |
| 1.777 | 34.026 | 19.144 | 85.225 |
| 3.161 | 36.949 | 11.689 | 52.037 |
| 5.621 | 40.711 | 7.243 | 32.242 |
| 9.996 | 45.649 | 4.567 | 20.330 |
| 17.777 | 51.678 | 2.907 | 12.942 |
| 31.612 | 59.979 | 1.897 | 8.447 |
| 56.207 | 71.348 | 1.269 | 5.651 |
| 99.950 | 86.330 | 0.864 | 3.845 |
| 177.750 | 106.240 | 0.598 | 2.661 |
| 316.100 | 136.750 | 0.433 | 1.926 |
| 562.150 | 173.290 | 0.308 | 1.372 |
| 999.640 | 224.550 | 0.225 | 1.000 |

| pH 3.5 PQ-37 and acrylamide | | | |
|---|---|---|---|
| Shear Rate (1/s) | Shear Stress (Pa) | Viscosity (Pas) | Visc/Visc@1000 s−1 |
| 0.001 | 3.171 | 3167.800 | 20175.785 |
| 0.002 | 5.632 | 3163.400 | 20147.761 |
| 0.003 | 5.880 | 1858.300 | 11835.552 |
| 0.006 | 6.029 | 1072.100 | 6828.228 |
| 0.010 | 6.262 | 626.550 | 3990.510 |
| 0.018 | 6.541 | 368.010 | 2343.863 |
| 0.032 | 6.937 | 219.430 | 1397.554 |
| 0.056 | 7.357 | 130.900 | 833.705 |
| 0.100 | 8.023 | 80.266 | 511.216 |
| 0.178 | 8.790 | 49.448 | 314.935 |
| 0.316 | 9.768 | 30.899 | 196.796 |
| 0.562 | 10.880 | 19.354 | 123.266 |
| 1.000 | 12.196 | 12.201 | 77.708 |
| 1.777 | 13.635 | 7.671 | 48.859 |
| 3.161 | 15.448 | 4.887 | 31.126 |
| 5.621 | 17.765 | 3.160 | 20.128 |
| 9.996 | 20.576 | 2.059 | 13.111 |
| 17.777 | 24.468 | 1.376 | 8.766 |
| 31.612 | 29.124 | 0.921 | 5.868 |
| 56.207 | 36.397 | 0.648 | 4.124 |
| 99.950 | 46.255 | 0.463 | 2.947 |
| 177.750 | 58.382 | 0.328 | 2.092 |
| 316.120 | 87.204 | 0.276 | 1.757 |
| 562.150 | 106.770 | 0.190 | 1.210 |
| 999.640 | 156.950 | 0.157 | 1.000 |

| pH 3.0 PQ-37 and acrylate | | | |
|---|---|---|---|
| Shear Rate (1/s) | Shear Stress (Pa) | Viscosity (Pas) | Visc/Visc@1000 s−1 |
| 0.001 | 6.410 | 6409.700 | 33602.621 |
| 0.002 | 12.218 | 6872.000 | 36026.212 |
| 0.003 | 14.156 | 4478.700 | 23479.423 |
| 0.006 | 14.690 | 2613.100 | 13599.083 |
| 0.010 | 15.247 | 1525.300 | 7996.330 |
| 0.018 | 15.901 | 894.500 | 4689.384 |
| 0.032 | 16.531 | 522.930 | 2741.442 |
| 0.056 | 17.382 | 309.220 | 1621.075 |
| 0.100 | 18.397 | 184.050 | 964.875 |
| 0.178 | 19.726 | 110.970 | 581.756 |
| 0.316 | 21.296 | 67.372 | 353.195 |
| 0.562 | 23.026 | 40.960 | 214.731 |
| 1.000 | 24.889 | 24.899 | 130.532 |
| 1.777 | 26.818 | 15.088 | 79.098 |
| 3.161 | 29.318 | 9.276 | 48.628 |
| 5.621 | 32.534 | 5.788 | 30.342 |
| 9.997 | 36.565 | 3.658 | 19.175 |
| 17.776 | 42.227 | 2.376 | 12.453 |
| 31.610 | 49.042 | 1.552 | 8.134 |
| 56.207 | 59.089 | 1.051 | 5.511 |
| 99.950 | 71.575 | 0.716 | 3.754 |
| 177.750 | 88.755 | 0.499 | 2.618 |
| 316.100 | 123.040 | 0.389 | 2.041 |
| 562.150 | 146.070 | 0.260 | 1.362 |
| 999.660 | 190.680 | 0.191 | 1.000 |

| pH 3.0 PQ-37 and acrylamide | | | |
|---|---|---|---|
| Shear Rate (1/s) | Shear Stress (Pa) | Viscosity (Pas) | Visc/Visc@1000 s−1 |
| 0.001 | 2.056 | 2058.600 | 16859.951 |
| 0.002 | 3.656 | 2056.700 | 16844.390 |
| 0.003 | 3.910 | 1237.100 | 10131.859 |
| 0.006 | 4.033 | 717.620 | 5877.314 |
| 0.010 | 4.232 | 423.360 | 3467.322 |
| 0.018 | 4.417 | 248.460 | 2034.889 |
| 0.032 | 4.630 | 146.490 | 1199.754 |
| 0.056 | 4.938 | 87.847 | 719.468 |
| 0.100 | 5.317 | 53.199 | 435.700 |
| 0.178 | 5.819 | 32.733 | 268.084 |
| 0.316 | 6.434 | 20.354 | 166.699 |
| 0.562 | 7.214 | 12.833 | 105.102 |
| 1.000 | 8.150 | 8.153 | 66.776 |
| 1.777 | 9.261 | 5.211 | 42.675 |
| 3.161 | 10.632 | 3.364 | 27.549 |
| 5.621 | 12.255 | 2.180 | 17.856 |
| 9.997 | 14.437 | 1.444 | 11.828 |
| 17.777 | 17.369 | 0.977 | 8.002 |
| 31.612 | 21.193 | 0.670 | 5.491 |
| 56.207 | 27.490 | 0.489 | 4.006 |
| 99.950 | 34.313 | 0.343 | 2.812 |
| 177.750 | 43.495 | 0.245 | 2.004 |
| 316.100 | 55.938 | 0.177 | 1.449 |
| 562.110 | 84.262 | 0.150 | 1.228 |
| 999.640 | 122.060 | 0.122 | 1.000 |

CONCLUSIONS

There is a clear benefit displayed from the PQ-37/acrylate copolymer over PQ-37/acrylamide copolymer (Tinovis CD) in all aspects of studied rheology Yield Stress is increased even when electrolyte is introduced by lowering the pH of the system.

Basic Shear profiles are maintained with some slight directional increase for the PQ-37/acrylate polymer.

The invention claimed is:

1. A hair treatment composition comprising a fatty alcohol-containing lamellar phase, an acid neutralized amidoamine surfactant, and a thickener which comprises a co-polymer derived from the polymerization of at least a non-ionic monomer (a) and at least a cationic monomer (b) and crosslinked, wherein the non-ionic monomer (a) is a poly(ethylene glycol) methacrylate of the following structure corresponding to Formula I:

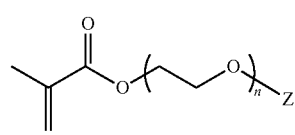

n is from 1 to 250 and Z is H or an alkyl group with 1 to 5 carbon atoms and wherein the cationic monomer (b) is a methacryloyloxyethyltrialkylammonium, quaternized or salified, wherein the cationic monomer represents from 85 to 99.9 mol% of the co-polymer, without taking into account any crosslinking agent or chain transfer agent that may be used in the polymerization, and wherein the hair treatment composition has a pH of from 2 to 6 and is in the form of a leave-on hair conditioner that contains no anionic surfactant.

2. Composition according to claim 1 wherein the non-ionic monomer (a) is poly(ethylene glycol) methacrylate.

3. Composition according to claim 1 wherein the cationic monomer (b) is methacryloyloxyethyltrialkylammonium salt of the following formula (II)

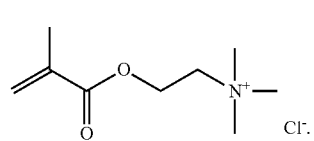

4. Composition according to claim 1 wherein the non-ionic monomer (a) represents the balance of the mol % of the polymer, without taking into account the crosslinking agent or the chain transfer agent.

5. Composition according to claim 1 wherein the copolymer is crosslinked with 50 to 5,000 ppm by weight of crosslinking agent based on the total amount of cationic and non-ionic monomers.

6. Composition according to claim 5 wherein the crosslinking agent is selected from the group comprising methylene bisacrylamide (MBA), ethylene glycol diacrylate, polyethylene glycol dimethacrylate, diacrylamide, cyanomethylacrylate, vinyloxyethylacrylate or methacrylate, triallylamine, formaldehyde, glyoxal, compounds of the glycidylether type and epoxy.

7. Composition according to claim 1 wherein the co-polymer is added to the composition in the form of an inverse emulsion made by reverse phase polymerisation.

8. Composition according to claim 7 wherein the inverse emulsion is concentrated by heating under vacuum to remove excess water and organic solvent by distillation.

9. Composition according to claim 1 comprising from 0.01 to 5% wt. of the composition of said thickener.

10. The composition according to claim 1 wherein the fatty alcohol is present in an amount of 0.01 to 5% by weight of the composition.

11. The composition according to claim 1 wherein the fatty alcohol comprises from 8 to 22 carbon atoms.

12. The composition according to claim 1 wherein the fatty alcohol comprises cetyl and/or stearyl alcohol.

13. The composition according to claim 1 wherein the acid neutralized amidoamine surfactant is of general formula:

$$R1\text{-}C(O)\text{—}NH\text{—}R2\text{-}N(R3)(R4)$$

wherein R1 is a fatty acid chain with from 12 to 22 carbon atoms, R2 is an alkylene group containing from one to 4 carbon atoms and R3 and R4 are, independently, an alkyl group having from one to four carbon atoms.

14. The composition of claim 1 further comprising a conditioning silicone.

* * * * *